United States Patent
Taniguchi et al.

(10) Patent No.: US 7,294,750 B2
(45) Date of Patent: Nov. 13, 2007

(54) ABSORBABLE PROTECTIVE COATINGS FOR WOUND WITH THE USE OF CELLULOSE SPONGE AND PROCESS FOR PRODUCING THE SAME

(75) Inventors: Kumiko Taniguchi, Tokyo (JP); Isao Kohno, Tokyo (JP); Koji Tanabe, Tokyo (JP); Yoshio Jo, Tokyo (JP); Isao Ohnishi, Tokyo (JP); Keisuke Kosake, Tokyo (JP); Yuri Koyama, Tokyo (JP)

(73) Assignee: Hogy Medical Co., Ltd., Tokyo (JP)

( * ) Notice: Subject to any disclaimer, the term of this patent is extended or adjusted under 35 U.S.C. 154(b) by 147 days.

(21) Appl. No.: 10/221,405

(22) PCT Filed: Sep. 4, 2001

(86) PCT No.: PCT/JP01/07631

§ 371 (c)(1),
(2), (4) Date: Mar. 14, 2003

(87) PCT Pub. No.: WO02/054998

PCT Pub. Date: Jul. 18, 2002

(65) Prior Publication Data

US 2004/0039322 A1 Feb. 26, 2004

(30) Foreign Application Priority Data

Jan. 12, 2001 (JP) .............................. 2001-522901

(51) Int. Cl.
*A61F 13/00* (2006.01)
(52) U.S. Cl. ......................................... 602/42; 602/45
(58) Field of Classification Search ............ 602/41–59; 604/180
See application file for complete search history.

(56) References Cited

U.S. PATENT DOCUMENTS 6,087,549 A * 7/2000 Flick ........................... 602/41

FOREIGN PATENT DOCUMENTS

| EP | 293208 | | 11/1988 |
| EP | 000837091 A1 | * | 4/1998 |
| JP | 2-160843 | | 6/1990 |
| JP | 3-109067 | | 5/1991 |
| JP | 0310967 A | * | 5/1991 |
| JP | 6-263911 | | 9/1994 |
| JP | 2000-254219 | | 9/2000 |
| WO | 94/16746 | | 8/1994 |

* cited by examiner

*Primary Examiner*—Kim M Lewis
(74) *Attorney, Agent, or Firm*—Dilworth & Barrese LLP

(57) ABSTRACT

An absorptive wound covering protecting material and a method for preparing an absorptive wound covering protecting material are characterized by solidifying a sponge raw solution containing no reinforcement that is obtained by mixing viscose and crystalline mirabilite as main raw materials, or a sponge raw solution obtained by mixing viscose containing a reinforcement comprising natural fibers having a length of at least 5 mm to 40 mm, and crystalline mirabilite as main raw materials, by performing a heat treatment on the sponge raw solution, and then forming the solidified cellulose sponge in a thickness somewhat greater than a desired thickness, and then forming the cellulose sponge in a sheet form having a desired thickness by compressing the cellulose sponge, and, if required, carboxymethylating hydroxyl groups in a glucose unit constituting a cellulose sponge so that a degree of substitution of the hydroxyl groups is from 0.5 to less than 1.0, and then, forming an incision the cellulose sponge.

7 Claims, 2 Drawing Sheets

ABSORBABLE PROTECTIVE COATINGS FOR WOUND WITH THE USE OF CELLULOSE SPONGE AND PROCESS FOR PRODUCING THE SAME

TECHNICAL FIELD

The present invention relates to an absorptive wound covering protecting material using a cellulose sponge that can be directly applied to a wound for the purpose of absorption of an exudate from the wound, and hemostatic cure and coating protection of the wound, and a method for preparing the same, particularly to an absorptive wound covering protecting material which can be directly applied to a drain tube insertion portion, a pin puncture portion, a tracheotomy tube insertion portion or the like into which a pin for an injury outside fixer, a drain tube or a tracheotomy tube is inserted, and a method for preparing the same.

BACKGROUND ART

As an absorptive covering protecting material applied to a wound, there is generally used a gauze for a medical use because it is thin and soft as well as highly bibulous, wherein the gauze is soft textile fabrics rough woven using yarn of cotton, silk or the like and, after weaving, is refined and bleached, and disinfected. For example, it is said that at a pin insertion portion into which a pin for an injury outside fixer is inserted, epidermal cells appear on a wound surface during five to seven days after an operation and fibroblasts produce collagen and various stroma so that blood vessels are actively regenerated. As a result, it is better to maintain the condition in which a pinhole is contracted with no infection and no scabs are observed, and it is also required to arrange a milieu in which an appropriate temperature, a humidity and an oxygen concentration can be maintained with no microorganisms, no foreign bodies and no necrotic tissues occurring in this stage. To meet these requirements, a so-called end-divided gauze which has an incision at a pin insertion portion is caught.

However, since an absorptiveness and a liquid-holding property of the gauze are insufficient, when an amount of an exudate from the wound is large, the exudate cannot be absorbed appropriately so that a leakage of the exudate occurs to make clothes, sheets or the like foul and unsanitary, or to cause too much trouble because the gauze has to be frequently exchanged in order to prevent the exudate from leaking. At the same time, scabs occur when the exudate is not absorbed into the gauze so that the regenerated cells may be unglued together with the scabs, or that autosensitization dermatitis may be caused by the exudate to delay the wound healing accompanied with eruptions or itching.

In addition, since drop-out fibers (lint) tend to occur from the above-mentioned gauze, the drop-out fibers easily adhere to the wound when the wound is directly covered with the gauze. Therefore, it is not preferable from the sanitary viewpoint to directly cover the wound with the gauze. Further, since the wound tends to be dried easily when using this gauze, the wound is often dried with the drop-out fibers attached to the wound, for example, when the end-divided gauze by the wound at the insertion portion of the pin for the injury outside fixer, at the insertion portion of the drain tube or the like, thereby making it extremely difficult to remove the end-divided gauze. Particularly, in the case that the wound is dried, not only the drop-out fibers separated from the gauze body but also the gauze body itself adheres to the wound and is dried. As a result, the regenerated cells with the scabs may be unglued when the gauze body is taken off from the wound, thereby bring a patient pain as well as causing a delay of the wound healing.

Furthermore, since the above-mentioned gauze is flexible, it cannot be fixed as it is. Therefore, a rubber sheet for press fixation has to be placed over the gauze in order to fix the gauze on the pin of an injury outside fixer. In this case, however, for example, if the wound has swollen, an impression caused by the rubber sheet for press fixation may remain as well as contact dermatitis might occur around the wound, so that the use of rubber sheet is not desirable.

Additionally, as for other absorptive wound covering protecting materials, use of a sponge of polyurethane or polyester has been considered, however, the sponge is not preferable in this case since its bibulousness is inferior and bullae occurs on the skin.

Therefore, as for an absorptive wound covering protecting material being excellent in an absorptiveness and a liquid-holding property without occurring drop-out fibers, which prevents a wound from being dried and besides has a certain shape-maintaining ability so as to make an attachment to the wound easy, and further can be directly applied to the wound, an absorptive wound covering protecting material has been proposed in Japanese Patent Number 3072596, that comprises a cellulose sponge characterized in that the cellulose sponge is prepared by performing a heat treatment in a prescribed temperature range on a sponge raw solution containing no reinforcement that is obtained by mixing viscose and crystalline mirabilite as main raw materials, so as to allow the sponge raw solution to be solidified in a thin thickness, so that the cellulose sponge is formed to be in a sheet form.

Although this material is the most preferable absorptive wound covering protecting material comprising the above-mentioned cellulose sponge so far as shown above, which is excellent in an absorptiveness and a liquid-maintaining ability with regard to the exudate from the wound, the material absorbs a large amount of exudate to degrade the shape-maintaining ability so that the material becomes flexible. As a result, when the absorptive wound covering protecting material is removed from the wound, it may be transformed so as to be difficult to operate. And besides, it is difficult for the absorptive wound covering protecting material to absorb a liquid with a high viscosity, although the material has a high absorptiveness to a liquid.

In addition, since the absorptive wound covering protecting material contains no reinforcement such as fibers and the like in order to prevent drop-out fibers from occurring, it is required to take care not to break the material when it is removed in a dried condition. Moreover, it cannot be denied that the material absorbs a larger amount of the exudate from the wound than necessary so that the strength of the material is reduced, and an attention should be paid not to break the absorptive wound covering protecting material when it is removed.

Furthermore, the absorptive wound covering protecting material only absorbs and maintains the exudate from the wound and it does not particularly enhance a hemostasis wound healing effect. For example, in the case that the amount of the exudate from the pin insertion portion of an injury outside fixer is especially large, it takes more days to be required for wound contraction at the pin insertion portion after an operation, compared to the case in which the amount of the exudate is small. However, since it is important that a pinhole at the pin insertion portion contracts as soon as possible after the operation so that the condition with no signs of infection is maintained, it has been desired to develop an absorptive wound covering protecting material which makes the wound contraction at the pin insertion portion be of excellent quality even in the case of a large amount of the exudate and besides has a certain shape-maintaining ability to make an attachment to the pin insertion portion of the injury outside fixer easy, and further can be directly applied to the wound.

DISCLOSURE OF THE INVENTION

The present invention is aimed to deal with such problems stated above. As a result of the thorough consideration for solving the problems, it has been found that an absorptive wound covering protecting material can be obtained which, as in the past, is excellent in an absorptiveness and a liquid-holding property without occurrence of drop-out fibers, with a wound being difficult to dry, and besides, which has a certain shape-maintaining ability so as to make an attachment to the wound easy, and, needless to say, which can be directly applied to the wound, and which is quite excellent in an absorptiveness and a liquid-holding property with a satisfactory shape-maintaining ability and strength as well as with an improved workability, by not only simply increasing an amount of the absorptive wound covering protecting material comprising the cellulose sponge disclosed in Japanese Patent Number 3072596 but also maintaining the shape in a certain initial shape, or by selecting a reinforcement to make it a specific shape even in the case of the absorptive wound covering protecting material comprising a cellulose sponge including the reinforcement such as fibers and the like.

That is, the present invention is an absorptive wound covering protecting material using a cellulose sponge is formed in a sheet form by compressing the cellulose sponge which is solidified by performing a heat treatment on a sponge raw solution containing no reinforcement that is obtained by mixing viscose and crystalline mirabilite as main raw materials, or an absorptive wound covering protecting material using a cellulose sponge is formed in a sheet form by compressing the cellulose sponge which has been solidified by performing a heat treatment on a sponge raw solution that is obtained by mixing viscose containing a reinforcement comprising natural fibers, and crystalline mirabilite as main raw materials. By directly applying and fixing such an absorptive wound covering protecting material to a wound so as to cover the wound, absorption of an exudate from the wound and protection of the wound can be achieved.

What has to be mentioned here is, in the case of containing the reinforcement, natural fibers such as cotton, hemp, silk, ramie, pulp and so on are used as a reinforcement because, when synthetic fibers such as rayon, nylon, polyester, polyethylene, polypropylene, acrylic, polystyrene, fluorine, latex, silicon and the like are used as a reinforcement, it is easy to slide and may cause drop-out fibers (lint). In addition, even using natural fibers, when the fibers have a length of 1 mm or less, they may drop out. Furthermore, when the fibers have a length of 50 mm or more, they may cause fiber lumps to occur so that they may not be uniformly mixed with raw materials while mixing. Thus, it is preferable to use natural fibers having a length from 5 mm to 40 mm.

Further, in the absorptive wound covering protecting material of the present invention, the crystalline mirabilite in a sponge raw solution containing a reinforcement of the above-stated the absorptive wound covering protecting material has a large particle size in order to improve an absorbtiveness to a fluid with a high viscosity. The particle size of the crystalline mirabilite is preferably in a range of 0.5 mm to 1.5 mm, and the mean particle size of 1 mm is appropriate.

In addition, in the absorptive wound covering protecting material of the present invention, a cellulose sponge is used which comprises natural or regenerated cellulose fibers wherein hydroxyl groups in a glucose unit constituting a cellulose molecule are partly carboxymethylated so that a degree of substitution (a degree of etherification) of the hydroxyl groups is from 0.5 to less than 1.0.

As stated above, by such a part carboxymethylation wherein a degree of substitution (a degree of etherification) of hydroxyl groups in a glucose unit is from 0.5 to less than 1.0 and by purification, the absorptive wound covering protecting material obtains an excellent absorptiveness to a tissue liquid such as blood and the like, and rapidly dissolves when contacting blood, and a hemostatic effect is shown by promoting an agglutination reaction of fibrin monomers to which fibrinogen is converted by thrombin which is finally activated by activation of a blood clot cascade.

That is, the absorptive wound covering protecting material does not promote the operation of the enzymes of the blood clot cascade at all, but promotes an agglutination of fibrin monomers prepared by thrombin and besides rapidly dissolves by contacting blood or body fluids from the wound so as to enhance adhesion and aggregation of blood platelet to the wound thereby interacting with fibrin or an adhesion protein, i.e., fibronectin at the wound so as to have an effect of promoting a cell adhesion activity of fibronectin.

Furthermore, the absorptive wound covering protecting material of the present invention may be varied in its shape according to its purpose (application site). For example, a mere thin sheet-shaped type without any incisions will do when using for the purpose of absorption of an exudate and protection at a wound, a bedsore, a burn area, a skin graft area and the like and absorption of an intestinal juice after providing an artificial anus or a urinary tract stoma. Moreover, when using for the purpose of absorption of an exudate and protection at a pin insertion portion of an injury outside fixer and absorption of an exudate and protection at a drain insertion portion, a cantilever-shaped injury outside fixer type (the above-stated thin sheet-shaped absorptive wound covering protecting material in which an incision is formed for insertion of a pin of an injury outside fixer or a drain tube) or a ring-shaped injury outside fixer type (the same sheet-shaped absorptive wound covering protecting material in which an incision and an insertion aperture are formed for insertion of a pin or a drain tube of an injury outside fixer) may be selected.

As for the absorptive wound covering protecting material in which the incision is formed, as shown in FIG. 2, for example, there can be devised an absorptive wound covering protecting material (1) obtained by forming an incision comprising a linear incision (2) which tends from an end portion (10a) of the cellulose sponge (10) to about a central portion, and an insertion aperture (3) which is partly notched in about the central portion (see (イ)), an absorptive wound covering protecting material (11) obtained by forming an incision comprising a linear incision (2) which tends from an end portion (10a) of the cellulose sponge (10) to about a central portion, and a radial incision (4) which spreads in at least two directions at about the central portion (see (ロ)) or an absorptive wound covering protecting material (21) obtained by forming an incision comprising an opening incision (5) which tends from an end portion (10*a*) of the cellulose sponge (10) to about a central portion, and an insertion aperture (3') which is partly notched in about the central portion (see (/\)). In addition to these, there can be devised an absorptive wound covering protecting material (31) obtained by forming an opening incision (5') which tends from an end portion (10*a*) of the cellulose sponge (10) to about a central portion, and a radial incision (4') which spreads in at least two directions at about the central portion (see (=)). Further, it is preferable to form a V-shaped introduction incision (6) on a side of the end portion (10*a*) of the cellulose sponge (10) in which the linear incision (2) is formed because a pin of an injury outside fixer or a drain tube can be introduced. Furthermore, a location, a number and a size of the incision formed in the cellulose sponge can be changed according to the application portion and the like as necessary.

And besides, an absorptive wound covering protecting material in which such an incision is formed, for example, the absorptive wound covering protecting material (1) in which an incision is formed as shown in FIG. 2 (イ), can be pushed into the injury outside fixer in such a way that the introduction incision (6) is fitted into a pin (P) of the injury outside fixer which is fixed at a leg portion (A), as shown in FIG. 1. This makes the incision (2) open easily so that the pin (P) is inserted into the aperture (3), then, the absorptive wound covering protecting material is attached in such a way that it covers the wound whereby it can absorb the exudate from the wound and cover and protect the wound.

In addition, an absorptive wound covering protecting material of the present invention is prepared by 1) solidifying a sponge raw solution containing no reinforcement that is obtained by mixing viscose and crystalline mirabilite as main raw materials, in a sheet form having a thickness somewhat greater than a desired thickness by performing a heat treatment in a temperature range of 35° C. to 70° C. on the sponge raw solution, and then forming the cellulose sponge in a sheet form having a desired thickness by compressing the solidified cellulose sponge, by 2) solidifying a sponge raw solution containing no reinforcement that is obtained by mixing viscose and crystalline mirabilite as main raw materials, in a sheet form having a thickness somewhat greater than a desired thickness by a first temperature maintaining process of performing a heat treatment in a temperature range of 35° C. to 70° C. on the sponge raw solution till the sponge raw solution loses a fluidity, and then completely solidifying the sponge raw solution by a second temperature maintaining process of subsequently performing a heat treatment in a temperature range of 90° C. to 100° C. on the solidified sponge raw solution, and then forming the cellulose sponge in a sheet form having a desired thickness by compressing the solidified cellulose sponge, or by 3) solidifying a sponge raw solution that is obtained by mixing viscose containing a reinforcement comprising natural fibers, preferably a reinforcement comprising natural fibers having at least a length of 5 mm to 40 mm, and crystalline mirabilite having a relatively large particle size, preferably crystalline mirabilite the particle size of which is in a range from 0.5 mm to 1.5 mm, as main raw materials, by performing a heat treatment in a temperature range of 75° C. to 90° C. on the sponge raw solution, and then slicing the solidified cellulose sponge in a thickness somewhat greater than a desired thickness, and then forming the cellulose sponge in a sheet form having a desired thickness by compressing the sliced cellulose sponge, respectively.

In addition, the compression of the cellulose sponge in the present invention is performed while applying heat to the cellulose sponge. By applying heat like this, the cellulose sponge is easily formed in a sheet form having a high density and a desired thickness. And as for the conditions such as a temperature and so on during the compression, the compression is preferably performed by applying a pressure of 6.0 MPa to 8.0 MPa at a temperature of 145° C. to 155° C. for 5 to 20 seconds. Additionally, for easy machining, the compression is preferably performed at two stages, that is, the deformation is corrected by a nip roller and the like at the first stage, and then the compression is performed to form a desired thickness which is aimed while applying heat at the second stage.

In addition, a soluble absorptive wound covering protecting material of the present invention comprises cellulose fibers wherein hydroxyl groups in a glucose unit constituting a cellulose molecule of a cellulose sponge are partly carboxymethylated so that a degree of substitution (a degree of etherification) of the hydroxyl groups is from 0.5 to less than 1.0, and the soluble absorptive wound covering protecting material is prepared by treating a compressed cellulose sponge with a sodium hydroxide aqueous solution, and then reacting the cellulose sponge with a monochloroacetic acid solution for a certain period of time, preferably for 4 to 18 hours, thereby partly carboxymethylating hydroxyl groups in a glucose unit constituting the cellulose sponge so that a degree of substitution (a degree of etherification) of the hydroxyl groups is from 0.5 to less than 1.0, and then purifying the cellulose sponge.

Moreover, in the preparing process of the soluble absorptive wound covering protecting material containing a reinforcement, natural fibers such as pulp, cotton and the like comprising cellulose which can receive the above-mentioned carbomethylating reaction as a component are used as a reinforcement. Therefore, the preferable soluble absorptive wound covering protecting material of the present invention can be represented as a structural unit which constitutes cellulose by a chemical formula shown as in the following formula.

[Chemical Formula 1]

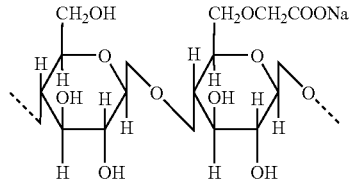

In addition, the soluble absorptive wound covering protecting material of the present invention is not limited to the one represented by the above chemical formula. Needless to say, any formula in included in the scope of the present invention if it has a soluble wound healing hemostatic effect that is aimed, being carboxymethylated (etherified) so that a degree of substitution of a hydroxyl group in a glucose unit constituting a cellulose molecule is from 0.5 to less than 1.0.

Here, a general method for preparing a cellulose sponge used in the present invention will be explained.

First, cellulose sponges containing no reinforcement are prepared respectively by mixing viscose with crystalline mirabilite and a polyol compound, and, if required, a surface active agent, and pouring the resulting sponge raw solution into a mold for molding, in a thickness somewhat greater than a desired thickness, and then performing a heat treatment at a relatively low temperature on the poured sponge raw solution, and then compressing the resultant product to form the cellulose sponge in a sheet form, or performing a heat treatment on the sponge raw solution by a first temperature maintaining process at a relatively low temperature and a second temperature maintaining process at a higher temperature than that of the first temperature maintaining process, and then compressing the resultant product to form the cellulose sponge in a sheet form having a desired thickness.

Further, the absorptive wound covering protecting material of the present invention using each of the above-described cellulose sponges may be used as it is prepared, and, if required (depending on application areas), may be prepared by providing an incision therein.

Additionally, in the case of the soluble absorptive wound covering protecting material of the present invention containing no reinforcement, the soluble absorptive wound covering protecting material is prepared by treating a cellulose sponge which is formed by compression in a sheet form having a desired thickness, with a sodium hydroxide aqueous solution, and then reacting the cellulose sponge with a monochloroacetic acid solution for a certain period of time, preferably for 4 to 18 hours, thereby partly carboxymethylating hydroxyl groups in a glucose unit constituting the cellulose sponge so that a degree of substitution (a degree of etherification) of the hydroxyl groups is from 0.5 to less than 1.0, and then purifying the partly carboxymethylated cellulose sponge. The soluble absorptive wound covering protecting material containing no reinforcement as prepared in such a manner may also be used as it is prepared, and, if required (depending on application areas), may be provided with an incision therein.

In the case of a cellulose sponge containing no reinforcement, as for viscose, it is industrially advantageous to typically use viscose for viscose rayon, and the viscose for viscose rayon is effectively available. As the viscose for viscose rayon, ordinary viscose, viscose for strong rayon, and the like may be used, and there is no limitation to the viscose for viscose rayon. A degree of polymerization of a cellulose component of the viscose is from 200 to 400, in particular, preferably from 250 to 350. The cellulose having a degree of polymerization of more than 400 is not preferable because the resulting sponge is hard. The cellulose having a degree of polymerization of less than 200 is not preferable because the resulting sponge is weak. Specifically, the viscose which has a cellulose concentration of 5 to 10 weight %, an alkali concentration of 3 to 8%, a Hottenroth value of 5 to 12, a falling ball viscosity of 20 to 300 sec/20° C. and a $\gamma$ value of 45 to 70, is preferably used.

The viscose having a cellulose concentration of less than 5 weight % is not preferable because the use of such viscose results in a low viscose viscosity so as to allow precipitation of crystalline mirabilite to occur in a sponge raw solution, so that the resulting sponge has nonuniform pores. On the contrary, the viscose having a cellulose concentration of more than 10 weight % is not preferable because the use of such viscose results in a high viscose viscosity so as to make it difficult to uniformly mix crystalline mirabilite in a sponge raw solution, so that the resulting cellulose sponge has nonuniform pores thereby making it impossible to obtain a cellulose sponge having a uniform flexibility and a uniform strength.

Additionally, any of the viscose having an alkali concentration of less than 3%, the viscose having a $\gamma$ value of less than 45 and the viscose having a Hottenroth value of less than 5 are not preferable because the use of such viscose makes a sponge raw solution easy to solidify, so that solidification of the sponge raw solution occurs during kneading operation of crystalline mirabilite into the sponge raw solution or when charging the sponge raw solution into a mold for molding. On the contrary, any of the viscose having an alkali concentration of more than 10%, the viscose having a $\gamma$ value of more than 70 and the viscose having a Hottenroth value of more than 12 are not preferable because the use of such viscose makes a sponge raw solution difficult to solidify, so that a solidification process of the sponge raw solution takes time.

Further, the viscose having a falling ball viscosity of less than 20 sec is not preferable for the same reason as stated above, because the use of such viscose results in too low a viscose viscosity so as to allow precipitation of crystalline mirabilite to occur in a sponge raw solution, so that the resulting sponge has nonuniform pores. On the contrary, the viscose having a falling ball viscosity of more than 300 sec is not preferable for the same reason as stated above, either, because the use of such viscose results in too high a viscose viscosity so as to make it difficult to uniformly mix crystalline mirabilite, so that the resulting sponge has nonuniform pores.

The mean particle size of crystalline mirabilite is preferably 0.2 mm or less, and more preferably, in the range of 0.01 mm to 0.2 mm. The crystalline mirabilite the mean particle size of which is more than 0.2 mm results in a larger diameter of the pores (cells) constituting the cellulose sponge so as to badly affect a contractivity in a dried condition and a swelling recovering ratio. In addition, variations in strength of the obtained cellulose sponges result.

Additionally, the addition amount of the crystalline mirabilite is a 50-fold to 100-fold amount, preferably a 60-fold to 80-fold amount (in weight ratio) with regard to the amount of the cellulose in the viscose.

When the addition amount of the crystalline mirabilite is less than a 50-fold weight amount with regard to the cellulose weight in the viscose, an apparent density when being dried becomes too high and cell walls become thick thereby resulting in loss of flexibility of the obtained sponge. In addition, it is not preferable that the addition amount be more than a 100-fold amount, because, if the addition amount is more than a 100-fold amount, the viscosity of the sponge raw solution becomes high in mixing operation so that the strength of the resultant sponge becomes too low.

By adding a surface active agent to the viscose, the fluidity of the sponge raw solution can be increased, that is, the viscosity can be appropriately lower, so that less air is involved when charging the sponge raw solution into a mold for molding so as to make it possible to improve workability as well as to obtain a cellulose sponge which is stable in quality such as strength, flexibility and the like. The addition of the surface active agent to the viscose may be performed when necessary. In the case of a sponge raw solution using viscose wherein a alkali concentration, a $\gamma$ value and a Hottenroth value are relatively high, the fluidity of the sponge raw solution is sufficiently high so that the addition of a surface active agent is not necessary.

As the above-stated surface active agent, an anionic surface active agent and/or a nonionic surface active agent can be used. A cationic surface active agent is not preferable because it denatures the viscose. Particularly preferable surface active detergents are one or more selected from sodium dodecyl sulfate and sorbitan monooleic acid ester and ethylene oxide addition products of these surface active agents (for example, sorbitan monooleic acid ester +20

($C_2H_4O$)). Any one of these surface active agents can be easily used if it is added to the viscose in advance.

The addition amount of the surface active agent is preferably 1.0 weight percent or less relative to the viscose. More preferably, it is within 0.02 to 1.0 weight percent, and most preferably, 0.1 to 1.0 weight percent. No effect of addition can be obtain when used in an amount of less than 0.02 weight percent.

In addition, since more effect cannot be seen even if the surface active agent is used in an amount of 1.0 weight percent or more, it is no use to add 1.0 weight percent or more. Further, when the surface active agents are solids, it is preferable that the surface active agents be mixed with the undermentioned polyethylene glycol in advance and that the mixture be then added.

Additionally, among well-known polyol compounds as an additive for the viscose, glycerin and the like cannot be used because it makes the sponge hard so that the sponge cannot be used, the reason for which is unknown. Furthermore, when adding polyethylene glycol to the viscose, it is preferable to add a part of the polyethylene glycol in advance, and then add the rest of the polyethylene glycol together with the surface active agent so that the addition amount can be adjusted.

A mixing of each of the above-stated raw materials is generally performed by mixing polyalkylene glycol with viscose first, and, if required, a surface active agent next, and finally crystalline mirabilite. Additionally, in this mixing process, a pigment or an X ray untransparent material such as barium sulfate and the like can also be mixed, if necessary. The mixing device is not particularly limited if it has a cooling mechanism with which a viscose temperature can be adjusted not to be 20° C. or more. If the viscose temperature is more than 20° C., the solidification of the viscose begins, and as a result, uniform pores are not easily formed. The addition and mixing of crystalline mirabilite, polyalkylene glycol and a surface active agent can be performed by mixing these three agents into viscose at the same time. However, it is preferable to add crystalline mirabilite to the viscose to which polyalkylene glycol and a surface active agent are added in advance.

On the other hand, cellulose sponges containing a reinforcement are prepared respectively by mixing viscose to which natural fibers as a reinforcement are added in advance and then which is matured, with crystalline mirabilite and a polyol compound, and, if required, a surface active agent, and charging with pressure the resulting sponge raw solution into a mold for molding, and performing a heat treatment at a relatively high temperature on the charged sponge raw solution, and then slicing the resultant cellulose sponge after the heat treatment in a thickness somewhat greater than a desired thickness, and then compressing the sliced cellulose sponge to form the cellulose sponge in a sheet form, or charging with pressure the resulting sponge raw solution into a mold for molding, in a thickness somewhat greater than a desired thickness, and performing a heat treatment at a relatively low temperature on the charged sponge raw solution, and then compressing the resultant product to form the cellulose sponge in a sheet form having a desired thickness. Moreover, the absorptive wound covering protecting material of the present invention using each of the above-stated cellulose sponges may be used as it is prepared, and, if required (depending on application areas), may be prepared by providing an incision therein.

In addition, in the case of the soluble absorptive wound covering protecting material of the present invention containing a reinforcement, the soluble absorptive wound covering protecting material is prepared by treating a cellulose sponge which is formed by compression in a sheet form having a desired thickness, with a sodium hydroxide aqueous solution, and then reacting the cellulose sponge with a monochloroacetic acid solution for a certain period of time, preferably for 4 to 18 hours, thereby partly carboxymethylating hydroxyl groups in a glucose unit constituting the cellulose sponge so that a degree of substitution (a degree of etherification) of the hydroxyl groups is from 0.5 to less than 1.0, and then purifying the partly carboxymethylated cellulose sponge. When preparing the soluble absorptive wound covering protecting material containing a reinforcement, it is necessary to use as a reinforcement, natural fibers such as pulp, cotton and the like comprising cellulose which can receive the carboxymethylating reaction as a component. The soluble absorptive wound covering protecting material containing a reinforcement as prepared in such a matter may also be used as it is prepared, and, if required (depending on application areas), may be provided with an incision therein.

In this case, it is preferable that the viscose comprise the cellulose component having a degree of polymerization of 600 to 700. The cellulose having a high degree of polymerization is not preferable because the viscose comprising such cellulose becomes hard and the solubility becomes worse. The cellulose having a low degree of polymerization is not preferable because the viscosity becomes too low. Specifically, the viscose which has a cellulose concentration of 6 to 9 weight %, an alkali concentration of 7.8 to 8%, a Hottenroth value of 8 to 10, a falling ball viscosity of 50 to 200 sec/20° C. and a γ value of 70 to 75, is preferably used.

Moreover, the viscose having a cellulose concentration of less than 5 weight % is not preferable because the use of such viscose results in a low viscose viscosity so as to allow precipitation of crystalline mirabilite to occur in a sponge raw solution, so that the resulting sponge has nonuniform pores. On the contrary, the viscose having a cellulose concentration of more than 10 weight % is not preferable because the use of such viscose results in a high viscose viscosity so as to make it difficult to uniformly mix crystalline mirabilite in a sponge raw solution, so that the resulting cellulose sponge has nonuniform pores thereby making it impossible to obtain a cellulose sponge having a uniform flexibility and a uniform strength.

Additionally, any of the viscose having an alkali concentration of less than 7.8%, the viscose having a γ value of less than 70 and the viscose having a Hottenroth value of less than 5 are not preferable because the use of such viscose makes a sponge raw solution easy to solidify, so that solidification of the sponge raw solution occurs during kneading operation of crystalline mirabilite into the sponge raw solution or when charging the sponge raw solution into a mold for molding. On the contrary, any of the viscose having an alkali concentration of more than 8%, the viscose having a γ value of more than 75 and the viscose having a Hottenroth value of more than 10 are not preferable because the use of such viscose makes a sponge raw solution difficult to solidify, so that a solidification process of the sponge raw solution takes time.

Further, the viscose having a falling ball viscosity of less than 20 sec is not preferable for the same reason as stated above, because the use of such viscose results in too low a viscose viscosity so as to allow precipitation of crystalline mirabilite to occur in a sponge raw solution, so that the resulting sponge has nonuniform pores. On the contrary, the viscose having a falling ball viscosity of more than 300 sec is not preferable for the same reason as stated above, either, because the use of such viscose results in too high a viscose viscosity so as to make it difficult to uniformly mix crystalline mirabilite, so that the resulting sponge has nonuniform pores.

The particle size of crystalline mirabilite may be similar to that in the case of cellulose sponge containing no reinforcement. However, in order to absorb easily even a liquid with a high viscosity, the particle size is particularly preferably in the range of 0.5 mm to 1.5 mm, and the mean particle size is appropriately 1 mm. The crystalline mirabilite the mean particle size of which is more than 5 mm results in a larger diameter of the pores (cells) constituting the cellulose sponge so as to badly affect a contractivity in a dried condition and swelling recovering ratio. In addition, variations in strength of the obtained cellulose sponges result.

Additionally, the addition amount of the crystalline mirabilite is a 60-fold to 100-fold amount, preferably a 75-fold to 85-fold amount (in weight ratio) with regard to the amount of the cellulose in the viscose.

When the addition amount of the crystalline mirabilite is less than 50-fold weight amount with regard to the cellulose weight in the viscose, an apparent density when being dried becomes too high and cell walls become thick thereby resulting in loss of flexibility of the obtained sponge. In addition, it is not preferable that the addition amount be more than a 100-fold amount, because, if the addition amount is more than a 100-fold amount, the viscosity of the sponge raw solution becomes high in mixing operation so that the strength of the resultant sponge becomes too low.

In addition, a surface active agent can be added when necessary in the same condition as in the case of the cellulose sponge containing no reinforcement.

A material of a mold can be essentially used if its heatproof temperature is 100° C. or more. For example, the mold can be made of stainless, plastic, glass or ceramic-plastic, or a material which is coated with Teflon and the like. Specifically, as for plastics, for example, PTFE, polopropylene, heatproof vinyl chloride, high density polyethylene and so on are preferable because they are available at a relatively low cost and besides, easy to take off from the mold.

In the case of the cellulose sponge containing no reinforcement, it is important in the present invention to perform a temperature maintaining process of maintaining the sponge raw solution which is charged into a mold, at a temperature of 35° C. or more and within 70° C. (within a first temperature range) for 30 minutes or more and within 24 hours. It is particularly preferable that the process be performed at a temperature of 35 to 45° C. for 60 minutes to 5 hours. Specifically, the sponge raw solution is maintained in the first temperature range till its fluidity is lost. If the first temperature range is lower than 35° C., the process takes too much time and it is not industrially applicable. In addition, if a heat treatment beyond 70° C. in a solidification process which is performed in a conventional preparation of a cellulose sponge is performed in the first temperature maintaining process, bubbles of carbon disulfide rapidly occur and the resulting cellulose sponge has nonuniform pores thereby making it impossible to obtain a cellulose sponge having a uniform flexibility. In addition, when the first temperature range is higher than 70° C., the solidification proceeds from circumferences thereby causing flaps at the parts abutting the mold and the resulting cellulose sponge has different strengths between an inside and a periphery so that it becomes unsuitable for medical use.

The sponge raw solution can be completely solidified at the above-mentioned first temperature maintaining process, but the solidification takes too much time thereby making the process industrially disadvantageous. Accordingly, it is industrially advantageous means to add a second temperature maintaining process, after the above-stated first temperature maintaining process, which comprises a high temperature heat treatment of 90° C. or more (a second temperature range) for subsequently maintaining within the range of 30 minutes to 5 hours the sponge raw solution solidified in the first temperature maintaining process, because the second temperature maintaining process enables to shorten the time for solidification. More preferably, the second temperature maintaining process is performed at a temperature of 90° C. or more and within 100° C. within the range of 1 hour to 4 hours. If the second temperature range is less than 90° C., the sponge after being taken off from the mold has difficult in having a delomorphous property. As a result, fluid absorptive ratios or wet strengths vary widely, thereby deteriorating the whole performance of the cellulose sponge for medical use. In addition, if a heat treatment performed in the second temperature maintaining process is not complete, the sponge raw solution which is not solidified yet can be eluted when washing with water thereby making the formation of the sponge insufficient.

In addition, the first temperature maintaining process and the second temperature maintaining process are not particularly restricted, if only the temperatures can be maintained uniformly. However, it is convenient to pour the sponge raw solution into a molding placed in warm water in order to perform the heat treatments uniformly and industrially.

On the other hand, when the sponge raw solution which was charged with pressure into a mold for molding is the cellulose sponge containing a reinforcement, it is important in the present invention to perform a temperature maintaining process of maintaining the charged sponge raw solution at a temperature of 75° C. or more and within 90° C. for 5 hours or more and within 8 hours. It is particularly preferable that the process be performed at a temperature of 80 to 85° C. for 6 hours to 8 hours. In this case, if the heat treatment is incomplete, portions of the solution cannot be solidified to remain liquid so that the formation of the sponge is insufficient. On the contrary, if the heat treatment is performed excessively, not only coloration occurs but also energy wastes, which are industrial disadvantages.

It is easy to unmold the solidified sponge from the mold because the sponge raw solution contracts when it is solidified. However, attention is necessary because narrowing or transforming of the sponge at this stage makes it memorize the shape as is narrowed or transformed.

In addition, aftertreatments comprising each process of a water washing process, an acid regeneration process, a desulfurization process, a bleaching process and a neutralization process are performed on the molded sponge obtained by the above-stated unmolding process. The water washing process is preferably performed by washing with high temperature water till the crystalline mirabilite which was added to the sponge raw solution is completely eluted, and then followed by washing with ordinary temperature water. By such water washing, the surface active agent is also removed as well as the crystalline mirabilite. When the crystalline mirabilite or the surface active detergent remains, the material becomes inappropriate for medical use.

Next, the acid regeneration process (a cellulose regeneration process) is performed by almost the same method as of a typical viscose rayon generation process, for example, by soaking the molded sponge after the above-stated washing treatment has finished, in a sulfuric acid aqueous solution with a sulfuric acid concentration of approximately 40 to 100 g/L. By this process, the viscose is completely regenerated to be cellulose. The particularly preferable range of the sulfuric acid concentration of the sulfuric acid aqueous solution for use is 50 to 90 g/L. If the concentration of the sulfuric acid aqueous solution is higher than 100 g/L, the surface of the resulting sponge may be rough. If the concentration of the sulfuric acid aqueous solution is lower than 40 g/L, the regeneration occurs slowly. The immersion time is preferably 2 to 30 minutes. If the duration is shorter than 2 minutes, complete regeneration cannot be reached. Even if the immersion is performed for 30 minutes or more, the regeneration will not proceed any more because it has already been completed. The temperature for the immersion is preferably 20 to 50° C.

The immersion performed at a temperature less than 20° C. is not preferable because such temperature makes the regeneration slow. On the contrary, the temperature more than 50° C. is not preferable because such temperature sometimes makes the surface of the obtained sponge rough.

In addition, the desulfurization process (an alkali rinsing process) is performed by treating the molded sponge which have undergone the above-stated acid regeneration process, with a sodium hydroxide aqueous solution or a sodium sulfide aqueous solution. By this treatment, it is possible to decrease the remaining sulfur content in the sponge. The treatment is performed by soaking the sponge in a mixed solution of a sodium hydroxide aqueous solution with a sodium hydroxide concentration of 1 to 4 g/L and a sodium sulfide aqueous solution with a sodium sulfide concentration of 0.5 to 2 g/L. If the sodium hydroxide concentration of the sodium hydroxide aqueous solution is lower than 1 g/L, or if the sodium sulfide concentration of the sodium sulfide aqueous solution is lower than 0.5 g/L, hardening cannot be obtained. Additionally, if the sodium hydroxide aqueous solution has a sodium hydroxide concentration of more than 4 g/L, or if the sodium sulfide aqueous solution has a sodium sulfide concentration of more than 2 g/L, the surface of the sponge sometimes becomes rough. The temperature of the immersion solution is preferably 40 to 80° C. The immersion time is preferably 10 to 60 minutes. If the temperature is lower than 40° C., or if the immersion time is shorter than 10 minutes, it is difficult to obtain the effect. On the other hand, if the temperature is higher than 80° C., or if the immersion time is longer than 60 minutes, the surface of the sponge sometimes becomes rough. Specifically, the sponge is treated by soaking it into a mixed solution of a sodium hydroxide aqueous solution with a sodium hydroxide concentration of 1 to 4 g/L and a sodium sulfide aqueous solution with a sodium sulfide concentration of 0.5 to 2.0 g/L at a temperature of 40° C. to 80° C. for 10 to 60 minutes.

Further, the bleaching process may be performed by soaking the molded sponge in a hydrogen peroxide aqueous solution or a sodium hypochlorite aqueous solution having a concentration of 0.1 to 3.0 g/L for 10 to 30 minutes at ordinary temperature. If the sodium hypochlorite concentration or the hydrogen peroxide concentration is lower than 0.1 g/L, the bleaching effect cannot be obtained. Moreover, if the sodium hypochlorite concentration or the hydrogen peroxide concentration is higher than 3 g/L, the surface of the sponge sometimes becomes rough. The temperature of the immersion solution is preferably 20 to 50° C.

The immersion time preferably 10 to 30 minutes. If the temperature is lower than 20° C., or if the immersion time is shorter than 10 minutes, it is difficult to obtain the bleaching effect. On the other hand, if the temperature is higher than 50° C., or if the immersion time is longer than 30 minutes, the surface of the sponge sometimes becomes rough.

In addition, a neutralization process is performed for rinsing the sponge with water and removing the chemical agents used in the bleaching process so that the chemical agents cannot remain, and then, the water is squeezed from the rinsed sponge by a nip roller and the like so that the water cannot remain in the sponge, and then, if necessary, the sponge is sliced in a thickness somewhat greater than a desired thickness by a vertical cutter, and then, the sponge is dried with warm wind at 45° C. to 50° C., and then, the dried sponge is compressed by applying a pressure of 6.0 MPa to 8.0 MPa at a temperature of 145° C. to 155° C. for 5 to 20 seconds. In this case, the sponge raw solution may be solidified first in a thickness somewhat greater than a desired thickness and then compressed.

Additionally, as shown in FIG. 1 and FIG. 2, if required, an incision which is suitable for the application portion (for example, an incision matched with the position between pins of an injury outside fixation) is formed by stamping with a die or cutting with a cutter or the like. In addition, if the temperature is too high when drying, the sponge can be extremely bent so that the subsequent processing becomes difficult. On the other hand, the temperature is too low when drying, the drying process is not industrially preferable because it takes too much time.

Figure 1:
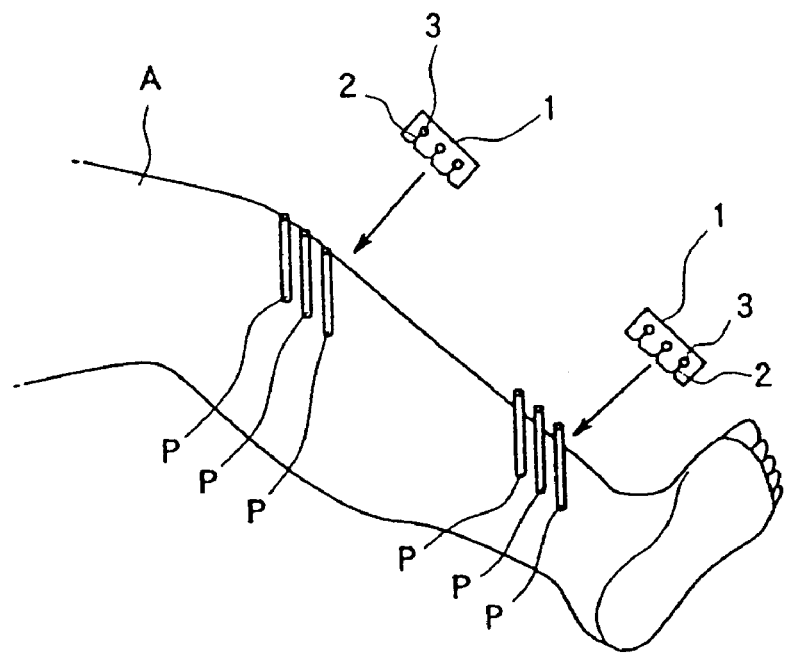
FIGS. 1 and 2 are depictions showing an application method of an absorptive wound covering protecting material of the present invention.

Explanation of Reference Numbers
A . . . a leg portion,
P . . . a pin of an injury outside fixation,
1, 11, 21, 31 and 41 . . . absorptive wound covering protecting materials,
2 . . . a line shaped incision,
3 and 3' . . . insertion apertures,
4 and 4' . . . radial incisions,
5 and 5' . . . opening incisions,
6 . . . an introduction incision,
10 . . . a cellulose sponge, and
10a . . . an end portion.

MODES FOR CARRYING OUT THE INVENTION

Specific preparation examples of an absorptive wound covering protecting material comprising a cellulose sponge containing no reinforcement of the present invention and effects thereof when being applied to a wound will be described below.

A preparation example of the absorptive wound covering protecting material is as follows. To viscose containing 6 weight % of alkali and 7 weight % of cellulose having a degree of polymerization of 320, polyethylene glycol having a mean molecular weight of 400 in an amount of 3 weight % relative to the viscose, sodium dodecyl sulfate in an amount of 0.4 weight % relative to the viscose and crystalline mirabilite having a mean particle size of 0.12 mm in a 65-fold amount by weight relative to the weight of the cellulose are added and mixed, whereby a sponge raw solution is prepared, and then, this sponge raw solution is charged into a dish-shaped container made of heat resistant polyvinyl chloride having an inner size of 200 mm×200 mm such that the thickness is about 10 mm which is somewhat greater than a desired thickness of 3 mm in the case of setting the desired thickness to be 3 mm. The solution is then subjected to a heat treatment wherein the solution is maintained in a water bath at 40° C. for 60 minutes, and subsequently maintained in a water bath at 90° C. for 120 minutes, whereby the solution is solidified, and then, the solidified product is taken off from the mold.

Next, mirabilite is removed from the released product with a boiling water at 90° C. or higher, and then the resulting sponge intermediate was soaked in a sulfuric acid aqueous solution of 50 g/L for 120 minutes to regenerate the cellulose, and further the regenerated sponge is soaked in a mixed solution of a sodium hydroxide aqueous solution with a sodium hydroxide concentration of 2.5 g/L and a sodium sulfide aqueous solution with a sodium sulfide concentration of 1.3 g/L at 50° C. for 10 minutes to perform a desulfurization treatment.

The desulfurized sponge is then soaked in a sodium hypochlorite aqueous solution having a sodium hypochlorite concentration of 0.2 g/L at ordinary temperature for 10 minutes to perform a desulfurization and bleaching treatment, and then the desulfurized and bleached sponge is washed with water and dried, and then, the dried sponge is compressed by applying a pressure of 8.0 MPa at a temperature of 150° C. such that the sponge can be in the desired thickness of 3 mm. The sponge is then cut into a suitable size for use and also an incision is formed therein in accordance with a pin of an injury outside fixer or a drain tube depending on an application portion whereby a rectangular sheet-shaped absorptive wound covering protecting material comprising a cellulose sponge was obtained.

Next, as comparative examples, in order to confirm the effect of the rectangular sheet-shaped absorptive wound covering protecting materials which are molded as stated above, when applying each of them to a wound, evaluations were made by measuring them against the conventional absorptive wound covering protecting materials comprising a sheet-shaped cellulose sponge without compressing, with regard to each of the following points of ① adhesion of sponge leavings, ② presence or absence of deformations ③ presence or absence of tears and ④ easiness in handling for changing, in the light of goodness or badness. The evaluation method is performed by rating on a scale of 1 to 3, namely, by selecting any of three ○ for good, Δ for no problems but not good, and × for problematic, the results of which are shown in the following [Table 1].

TABLE 1

| Form/Application Portion | Comparison Points | The product of the Present invention | | The conventional products | |
| --- | --- | --- | --- | --- | --- |
| | | Evaluation | Comments | Evaluation | Comments |
| Sheet-shaped Type / Gluteal region | ① Adhesion of sponge leavings | ○ | Completely None | Δ | Sometimes adhered |
| | ② Presence or absence of deformations | ○ | Completely None | Δ | Sometimes deformed |
| | ③ Presence or absence of tears | ○ | Completely None | ○ | Sometimes torn unless caution taken |
| | ④ Easiness in handling for changing | ○ | Good to put on and off | Δ | Good to put on and off |
| Cantilever Injury outside Fixation type / Right upper Arm | ① Adhesion of sponge leavings | ○ | Completely None | Δ | Sometimes adhered |
| | ② Presence or absence of deformations | ○ | Completely None | Δ | Sometimes deformed |
| | ③ Presence or absence of tears | ○ | Completely None | Δ | Sometimes torn unless caution taken |
| | ④ Easiness in handling for changing | ○ | Good to put on and off | Δ | Somewhat difficult to put on and off |
| Ring injury Outside Fixation type / Right lower leg | ① Adhesion of sponge leavings | ○ | Completely None | Δ | Sometimes adhered |
| | ② Presence or absence of deformations | ○ | Completely None | Δ | Sometimes deformed |
| | ③ Presence of absence of | ○ | Completely None | Δ | Sometimes torn when twisting |

TABLE 1-continued

| Form/Application Portion | Comparison Points | The product of the Present invention | | The conventional products | |
|---|---|---|---|---|---|
| | | Evaluation | Comments | Evaluation | Comments |
| | tears | | | | |
| | ④ Easiness in handling for changing | ○ | Good to put on and off | Δ | Somewhat difficult to put on and off |

As shown in the above-described [Table 1], the absorptive wound covering protecting material of the present invention not only has no adhesion of sponge leaving to the wound but also has a good absortiveness to an exudate, and moreover there are neither deformations nor tears in the absorptive wound covering protecting material thereby surely protecting its shape-maintaining ability, whereby it is found to be superior in all of the points of ② presence of absence of deformations, ③ presence or absence of tears and ④ easiness in handling for changing and to be far superior in an absorbtiveness to an exudate, to the conventional absortive wound covering protecting material without being compressed.

Next, specific preparation examples of the absorptive wound covering protecting material comprising a cellulose sponge containing a reinforcement of the present invention and effects thereof when being applied to wound will be described below.

A preparation examples of the absorptive wound covering protecting material is as follows. First, pulp having a degree of polymerization of 1000 is soaked into an 18.8 percent sodium hydroxide (NaOH) for 1 hour to make it swell, and then, the swollen pulp is ground, and then the ground pulp is aged by reacting it with oxygen in air at 18° C. for 12 hours. At this stage, if the temperature is lower, the degree of polymerization of cellulose is not sufficiently low so that the sponge becomes hard, and if the temperature is higher, the degree of polymerization is too low so that the sponge has a low strength and becomes brittle. Next to this stage, the resultant aged pulp is reacted with carbon disulfide in air to form sodium cellulose xanthate, and then, to the resulting xanthate, water, sodium hydroxide and a reinforcement comprising cotton having a fiber length of 20 mm are added and dissolved in a alkali concentration of 7.8 percent to form viscose. The viscose prepared as in this manner contains 8 weight % of cellulose having a degree of polymerization of 500 and 8 weight % of alkali.

The viscose prepared as described above is aged at 18° C. for 10 hours. To the aged viscose, polyethylene glycol having a mean molecular weight of 500 in an amount of 4 weight % relative to the viscose, sodium dodecyl sulfate in an amount of 0.5 weight % relative to the viscose and crystalline mirabilite having a mean particle size of 1 mm in a 70-fold amount by weight relative to the weight of the cellulose are then added and mixed whereby a sponge raw solution is obtained. In this process, if the aging temperature of the viscose is higher than 20° C., the solidification of the viscose starts thereby making it difficult to form uniform sponge pores.

This sponge raw solution is then charged with pressure at a back pressure of 3 kg into a mold for molding made of SUS304 according the JIS standard having an inner size of 600 mm×150 mm×100 mm while compressing. The solution is subjected to a heat treatment wherein the solution is maintained in a water bath at 80° C. for 6 hours, whereby the solution is solidified, and then, the solidified product is taken off from the mold.

Next, mirabilite is removed from the released from the released product with a warm water at 70° C. or higher, and then the resulting sponge intermediate is soaked in a sulfuric acid aqueous solution of 50 g/L for 120 minutes to regenerate the cellulose, and further the regenerated sponge is soaked in a mixed solution of a sodium hydroxide aqueous solution with a sodium hydroxide concentration of 2.5 g/L and sodium sulfide aqueous solution with a sodium sulfide concentration of 1.3 g/L at 50° C. for 10 minutes to perform a desulfurization treatment. Furthermore, the desulfurized sponge is soaked in a sodium hypochlorite aqueous solution having a sodium hyopchlorite concentration of 0.2 g/L at ordinary temperature for 10 minutes to perform a desulfurization and bleaching treatment, and then washing with water and drying were repeatedly performed three times on the desulfurized and bleached.

Moreover, the dried sponge is subjected to an oxalic acid treatment, and then the sponge is sliced in a thickness of about 10 mm which is somewhat greater than a desired thickness of 3 mm in the case of setting the desired thickness to be 3 mm, and then the sliced sponge is dried with a warm wind at 48° C., and then deformation is corrected by a nip roller, and then the corrected sponged is compressed by applying a pressure of 70 t at temperature of 150° C. such that the sponge can be in the desired thickness of 3 mm. Further, the sponge is then cut into a suitable size for use and also an incision is formed therein in accordance with a pin of an injury outside fixer or a drain tube depending on an application portion whereby a rectangular sheet-shaped absorptive wound covering protecting material comprising a cellulose sponge is obtained.

Next, as comparative examples, in order to confirm the effect of the rectangular sheet-shaped absorptive wound covering protecting materials which are molded as stated above, when applying each of them to a wound, evaluations were made by measuring them against the above-described absorptive wound covering protecting materials comprising a sheet-shaped cellulose sponge containing no reinforcement which is compressed, with regard to each of the following points of ① adhesion of drop-out fibers, ② presence or absence or deformations ③ presence or absence of tears and ④ easiness in handling for changing, in the light of goodness or badness. The evaluation method is performed by rating on a scale of 1 to 3, namely, by selecting any of three ○ for good, Δ for no problems but not good, and × for problematic, the results of which are shown in the following [Table 2].

|  |  | The product of the Present invention (with reinforcements) |  | The product of the Present invention (without reinforcement) |  |
| --- | --- | --- | --- | --- | --- |
| Form / Application Portion | Comparison Points | Evaluation | Comments | Evaluation | Comments |
| Sheet-shaped Type / Gluteal region | ① Adhesion drop-out fibers | ○ | Completely None | ○ | Completely None |
|  | ② Presence or absence of deformations | ○ | Completely None | ○ | Sometimes deformed depending on the state of exudates |
|  | ③ Presence or absence of tears | ○ | Completely None | ○ | Sometimes torn depending on handling, thus, caution required |
|  | ④ Easiness in handling for changing | ○ | Good to put on and off | ○ | Takes time relatively |
| Cantilever Injury outside Fixation type / Right upper Arm | ① Adhesion of drop-out fibers | ○ | Completely None | ○ | Completely None |
|  | ② Presence or absence of deformations | ○ | Completely None | ○ | Sometimes deformed depending on the state of exudates |
|  | ③ Presence or absence of tears | ○ | Completely None | ○ | Sometimes torn depending on handling, thus, caution required |
|  | ④ Easiness in handling for changing | ○ | Good to put on and off | ○ | Takes time relatively |
| Ring injury Outside Fixation type / Right lower leg | ① Adhesion of drop-out fibers | ○ | Completely None | ○ | Completely None |
|  | ② Presence or absence of deformations | ○ | Completely None | ○ | Sometimes deformed depending on the state of exudates |
|  | ③ Presence of absence of tears | ○ | Completely None | ○ | Sometimes torn depending on handling, thus, caution required |
|  | ④ Easiness in handling for changing | ○ | Good to put on and off | ○ | Takes time relatively |

As shown in the above-described [Table 2], being similar to the absorptive wound covering protecting material containing no reinforcement, the absorptive wound covering protecting material containing a reinforcement of the present invention not only has no adhesion of drop-out fibers to the wound but also has a good absorptiveness to an exudate, and moreover there are neither deformations, nor tears in the absorptive wound covering protecting material thereby surely protecting its shape-maintaining ability, and besides, it is found to be greatly superior in all of the points of ② presence or absence of deformations ③ presence or absence of tears and ④ easiness in handling for changing to the absorptive wound covering protecting material containing no reinforcement.

Next, specific preparation examples of the soluble absorptive wound covering protecting material comprising a cellulose sponge containing no reinforcement of the present invention will be described below.

First, as in the above-described manners, a compressed cellulose sponge containing no reinforcement is prepared. That is, to viscose containing 6 weight % of alkali and 7 weight % of cellulose having a degree of polymerization of 320, polyethylene glycol having a mean molecular weight of 400 in an amount of 3 weight % relative to the viscose, sodium dodecyl sulfate in an amount of 0.4 weight % relative to the viscose and crystalline mirabilite having a mean particle size of 0.12 mm in a 65-fold amount by weight relative to the weight of the cellulose are added and mixed, whereby a sponge raw solution is prepared, and then, this sponge raw solution is charged into a dish-shaped container made of heat resistant polyvinyl chloride having an inner size of 200 mm×200 mm such that the thickness is about 10 mm which is somewhat greater than a desired thickness of 3 mm in the case of setting the desired thickness to be 3 mm. The solution is then subjected to a heat treatment wherein the solution is maintained in a water bath at 40° C. for 60 minutes, and subsequently maintained in a water bath at 90° C. for 120 minutes, whereby the solution is solidified, and then, the solidified product is taken off from the mold.

Next, mirabilite is removed from the released product with a boiling water at 90° C. or higher, and then the resulting sponge intermediate is soaked in a sulfuric acid aqueous solution of 50 g/L for 120 minutes to regenerate the cellulose, and further the regenerated sponge was soaked in a mixed solution of a sodium hydroxide aqueous solution with a sodium hydroxide concentration of 2.5 g/L and a sodium sulfide aqueous solution with a sodium sulfide concentration of 1.3 g/L at 50° C. for 10 minutes to perform a desulfurization treatment.

The desulfurized sponge is then soaked in a sodium hypochlorite aqueous solution having a sodium hypochlorite concentration of 0.2 g/L at ordinary temperature for 10 minutes to perform a desulfurization and bleaching treatment, and then the desulfurized and bleached sponge is washed with water and dried, and then, the dried sponge is compressed by applying a pressure of 8.0 MPa at a temperature of 150° C. such that the sponge can be in the desired thickness of 3 mm.

Into a 3000 mL rotary reaction vessel, 40 g of the compressed cellulose sponge containing no reinforcement prepared in this way was put, and 1500 mL of an ethanol solution of sodium hydroxide comprising 37 volumes of a 46% sodium hydroxide aqueous solution and 63 volumes of 95% ethanol were then added to the sponge, and well infiltrated into it, and the mixture was stirred at 25° C. for 2 hours. Next, to this reaction solution, 900 mL of a monochloroacetic acid reactive solution wherein 300 of monochloroacetic acid was dissolved in 450 mL of 99.5% ethanol, was added and the reaction solution was stirred at 50° C. approximately for 4 to 18 hours. After termination of the reaction, a hydrogen ion concentration (pH) of the obtained solution containing a cellulose sponge was adjusted to 7.0 with 20% hydrochloric acid, and further the cellulose sponge was washed with a 70 to 95% ethanol aqueous solution till the content of NaCl in the cellulose sponge became 1% or less. The cellulose sponge treated in such a way was dried, and further, the sponge was cut into a suitable size for use and also an incision was formed therein in accordance with a pin of an injury outside fixer or a drain tube depending on an application portion, and then the sponge was sterilized to obtain a rectangular sheet-shaped soluble absorptive wound covering protecting material comprising a cellulose sponge containing no reinforcement.

Furthermore, as a test example 1, in order to check that a degree of substitution (a degree of etherification) of carboxymethyl groups of the soluble absorptive wound covering protecting material obtained by the above-stated means is 0.5 to less than 1.0, measurements of the degree of etherification corresponding to the stirring time with a monochloroacetic acid reactive solution were performed respectively. The measuring methods were as follows. In the above-stated examples, each 1 g of the soluble absorptive wound covering protecting materials prepared by stirring with the monochloroacetic acid reactive solution for 2, 4, 8, 14 and 18 hours respectively was cut into pieces and put into a ground Erlenmeyer flask (50 mL), and 25 mL of a nitric acid methanol solution (a mixed solution of 100 mL of methanol and 10 mL of nitric acid) was added to the material, and the mixture was shaken for 1 hour. Next, the sample was trapped by suction filtration with a glass filter (G3) and it was rinsed with 120 mL (40 mL×3 times) of a 800 g/L methanol solution (a mixed solution of 100 mL of absolute methanol and 20 mL of water). Finally, it was rinsed with 25 mL of absolute methanol, and then filtered with suction, and the sample on the filter was dried at 105° C. for 2 hours. Further, 0.2 g of the sample which became a hydrogen type was precisely weighed, and put into a ground Erlenmeyer flask (100 mL), and 8 mL of a 800 g/L methanol and 20 mL of a 0.1 mol/L sodium hydroxide standard solution were added to the sample, and the mixture was shaken at 25° C. for 30 minutes so as to allow the hydrogen type sample to be a sodium type sample. And then, an excess amount of sodium hydroxide was determined by titration with 0.05 mol/L sulfuric acid having a known normality using phenolphthalein as an indicator. The results of the measurement are shown in [Table 3].

TABLE 3

| Number of the soluble absorptive wound covering protecting material | A degree of etherification (a degree of substitution of a carboxymethyl group) Stirring reaction time (hours) | | | | |
|---|---|---|---|---|---|
| | 2 | 4 | 8 | 14 | 18 |
| 1 | 0.455 | 0.673 | 0.798 | 0.923 | 0.985 |
| 2 | 0.473 | 0.685 | 0.808 | 0.930 | 0.990 |
| 3 | 0.467 | 0.690 | 0.815 | 0.936 | 0.981 |

As shown in the results of the above-described [Table 3], the soluble absorptive wound covering protecting material having a degree of substitution of 0.5 or more can be prepared in a condition that a reaction time with monochloroacetic acid is about 4 hours or more. Accordingly, it is found that a degree of substitution of a carboxymethyl group can be controlled by controlling the reaction time with monochloroacetic acid.

Next, specific preparation examples of the soluble absorptive wound covering protecting material comprising a cellulose sponge containing a reinforcement of the present invention will be described below.

First, as stated above, a compressed cellulose sponge containing a reinforcement is prepared. That is, pulp having a degree of polymerization of 1000 is soaked into an 18.8 percent sodium hydroxide (NaOH) for 1 hour to make it swell, and then, the swollen pulp is ground, and then the ground pulp is aged by reacting it with oxygen in air at 18° C. for 12 hours. At this stage, if the temperature is lower, the degree of polymerization of cellulose is not sufficiently low so that the sponge becomes hard, and if the temperature is higher, the degree of polymerization is too low so that the sponge has a low strength and becomes brittle. Next to this stage, the resultant aged pulp is reacted with carbon disulfide in air to form sodium cellulose xanthate, and then, to the resulting xanthate, water, sodium hydroxide and a reinforcement comprising cotton having a fiber length of 20 mm are added and dissolved in a alkali concentration 7.8 percent to form viscose. The viscose prepared as in this manner contains 8 weight % of cellulose having a degree of polymerization of 500 and 8 weight % of alkali.

The viscose prepared as described above is aged at 18° C. for 10 hours. To the aged viscose, polyethylene glycol having a mean molecular weight of 500 in an amount of 4 weight % relative to the viscose, sodium dodecyl sulfate in an amount of 0.5 weight % relative to the viscose and crystalline mirabilite having a mean particle size of 1 mm in a 70-fold amount by weight relative to the weight of the cellulose are then added and mixed whereby a sponge raw solution is obtained. In this process, if the aging temperature of the viscose is higher than 20° C., the solidification of the viscose starts thereby making it difficult to form uniform sponge pores.

This sponge raw solution is then charged with pressure at a back pressure of 3 kg into a mold for molding made of SUS304 according the JIS standard having an inner size of 600 mm×150 mm×100 mm while compressing. The solution is subjected to a heat treatment wherein the solution is maintained in a water bath at 80° C. for 6 hours, whereby the solution is solidified, and then, the solidified product is taken off from the mold.

Next, mirabilite is removed from the released product with a warm water at 70° C. or higher, and then the resulting sponge intermediate is soaked in a sulfuric acid aqueous solution of 50 g/L for 120 minutes to regenerate the cellulose, and further the regenerated sponge is soaked in a mixed solution of a sodium hydroxide aqueous solution with a sodium hydroxide concentration of 2.5 g/L and a sodium sulfide aqueous solution with a sodium sulfide concentration of 1.3 g/L at 50° C. for 10 minutes to perform a desulfurization treatment. Furthermore, the desulfurized sponge is soaked in a sodium hypochlorite aqueous solution having a sodium hypochlorite concentration of 0.2 g/L at ordinary temperature for 10 minutes to perform a desulfurization and bleaching treatment, and then washing with water and drying were repeatedly performed three times on the desulfurized and bleached.

Moreover, the dried sponge is subjected to an oxalic acid treatment, and then the sponge is sliced in a thickness of about 10 mm which is somewhat greater than a desired thickness of 3 mm in the case of setting the desired thickness to be 3 mm, and then the sliced sponge is dried with a warm wind at 48° C., and then deformation is corrected by a nip roller, and then the corrected sponge is compressed by applying a pressure of 70 t at temperature of 150° C. such that the sponge can be in the desired thickness of 3 mm.

Into a 3000 mL rotary reaction vessel, 40 g of the compressed cellulose sponge containing a reinforcement prepared in this way was put, and 1500 mL of an ethanol solution of sodium hydroxide comprising 37 volumes of a 46% sodium hydroxide aqueous solution and 63 volumes of 95% ethanol were then added to the sponge, and well infiltrated into it, and the mixture was stirred at 25° C. for 2 hours. Next, to this reaction solution, 900 mL of a monochloroacetic acid reactive solution wherein 300 of monochloroacetic acid was dissolved in 450 mL of 99.5% ethanol, was added and the reaction solution was stirred at 50° C. approximately for 4 to 18 hours. After termination of the reaction, a hydrogen ion concentration (pH) of the obtained solution containing a cellulose sponge was adjusted to 7.0 with 20% hydrochloric acid, and further the cellulose sponge was washed with a 70 to 95% ethanol aqueous solution till the content of NaCl in the cellulose sponge became 1% or less. The cellulose sponge treated In such a way was dried, and further, the sponge was cut into a suitable size for use and also an incision was formed therein in accordance with a pin of an injury outside fixer or a drain tube depending on an application portion, and then the sponge was sterilized to obtain a rectangular sheet-shaped soluble absorptive wound covering protecting material comprising a cellulose sponge containing a reinforcement.

Furthermore, as a test example 2, in order to check that a degree of substitution (a degree of etherification) of carboxymethyl groups of the soluble absorptive wound covering protecting material obtained by the above-stated means is 0.5 to less than 1.0, measurements of the degree of etherification corresponding to the stirring time with a monochloroacetic acid reactive solution were performed respectively. The measuring methods were performed in a manner similar to those in the test example 1 stated in the examples relating to the preparation of the above-stated rectangular sheet-shaped soluble absorptive wound covering protecting material comprising a cellulose sponge containing no reinforcement. The results of the measurement are shown in [table 4].

TABLE 4

| Number of the soluble absorptive wound covering protecting material | A degree of etherification (a degree of substitution of a carboxymethyl group) Stirring reaction time (hours) | | | | |
|---|---|---|---|---|---|
| | 2 | 4 | 8 | 14 | 18 |
| 1 | 0.462 | 0.680 | 0.811 | 0.932 | 0.987 |
| 2 | 0.458 | 0.682 | 0.807 | 0.921 | 0.974 |
| 3 | 0.470 | 0.674 | 0.823 | 0.922 | 0.969 |

As shown in the results of the above-described [Table 4], the soluble absorptive wound covering protecting material having a degree of substitution of 0.5 or more could be prepared in a condition that a reaction time with monochloroacetic acid is about 4 hours or more, as in the case of the above-stated rectangular sheet-shaped soluble absorptive wound covering protecting material comprising a cellulose sponge containing no reinforcement. Accordingly, in the case of a cellulose sponge containing a reinforcement, it was found that a degree of substitution of a carboxymethyl group can be controlled by controlling the reaction time with monochloroacetic acid, too.

Next, as a test example 3, in order to check solubility of the soluble absorptive wound covering protecting material of the present invention, solubility to 0.95% brine and to pure water of the soluble absorptive wound covering protecting material comprising a cellulose sponge containing a reinforcement prepared in the above-stated embodiments (whose reaction time with monochloroacetic acid is 14 hours) was measured. As a measuring method, 1 g of the soluble absorptive wound covering protecting material (so as to be 1 w/v %) was added to 100 mL of 0.95% brine and water, and while stirring at 25° C., the time till insoluble materials disappear was visually observed. The results of the measurement are shown in [Table 5].

TABLE 5

| Number of the soluble absorptive wound covering protecting material | Time to be dissolved (minutes) | |
|---|---|---|
| | Pure water | 0.95% brine |
| 1 | 40 | 62 |
| 2 | 38 | 64 |
| 3 | 38 | 61 |
| 4 | 41 | 63 |
| 5 | 39 | 64 |

As shown in the results of the above-described [Table 5], it is found that the soluble absorptive wound covering protecting material of the present invention can be surely and rapidly dissolved completely both in water and in brine. That is, even in the case of containing a reinforcement, by selecting the reinforcement comprising cellulose, the reinforcement can be carboxymethylated and it can surely be dissolved both in water and in brine. Therefore, when applying a soluble absorptive wound covering protecting material to a wound, there is no possibility that insoluble foreign bodies remain which might bring the danger of causing inflammation and the like of the wound.

Figure 2:
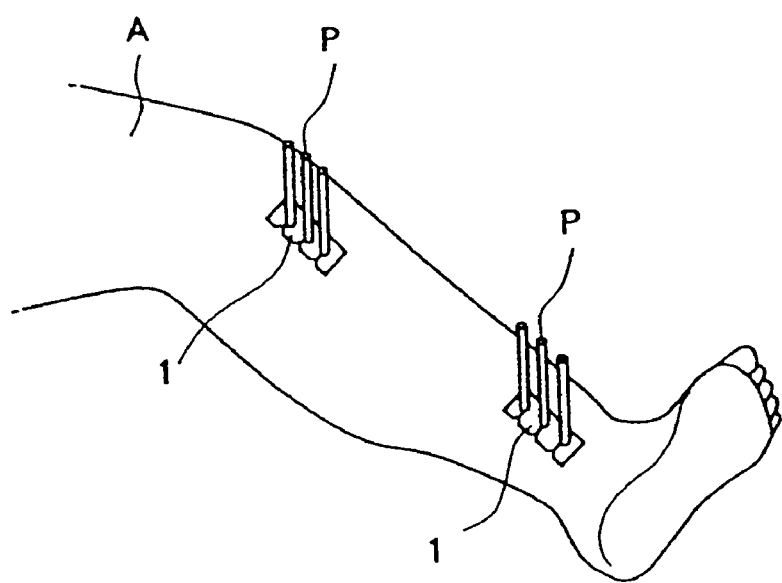
Figure 2A:
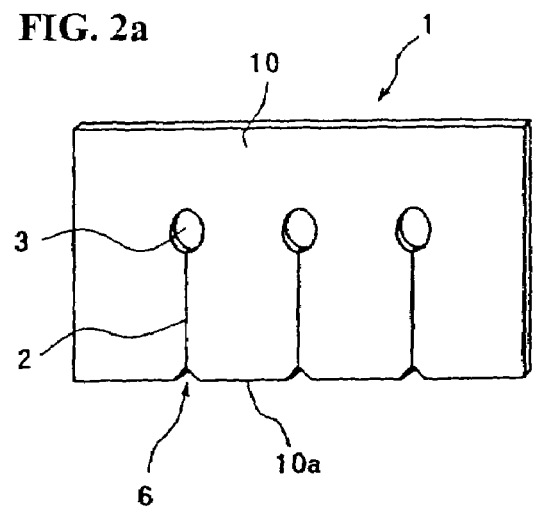
FIG. 2a is a front view showing an absorptive wound covering protecting material having an incision of the present invention.
Figure 2B:
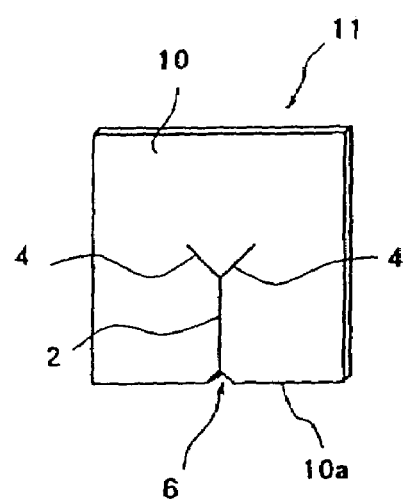
FIG. 2b is a front view showing another absorptive wound covering protecting material having an incision of the present invention.
Figure 2C:
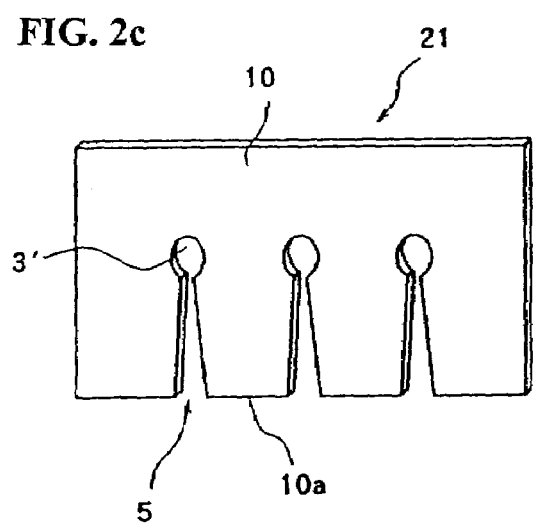
FIG. 2c is a front view showing another absorptive wound covering protecting material having an incision of the present invention.
Figure 2D:
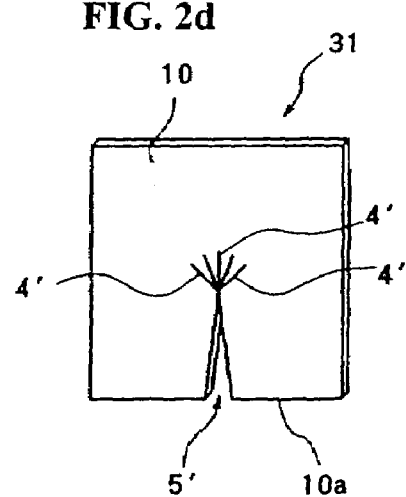
FIG. 2d is a front view showing another absorptive wound covering protecting material having an incision of the present invention.
Figure 2E:
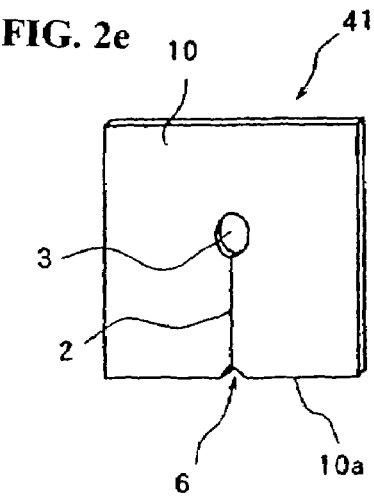
FIG. 2e is a front view showing another absorptive wound covering protecting material having an incision of the present invention.

Next, as a test example 4, the soluble absorptive wound covering protecting material comprising a cellulose sponge containing a reinforcement of the present invention was examined with regard to its hemostatic effect and wound healing effect when applying it to a pin insertion portion in an experimental injury outside fixation using four beagles. An injury outside fixer was attached to the left shinbone of beagles under general anesthesia, and then, osteotomy was performed on the diaphysial portion. After the operation, as shown in FIG. 2 (◻), a proximal or distal pin insertion portion was covered with the soluble absorptive wound covering protecting material having a Y-shaped slit (each n=2). As a control, an absorptive wound covering protecting material comprising a sheet-shaped compressed cellulose sponge containing a reinforcement was used. After the pin insertion portions were covered respectively in this way, they were protected by laying a bandage over them along with the injury outside fixer, and the first bandage exchange was performed two or three days after the surgery, which was followed by the second bandage exchange performed five to seven days after the surgery. Further, every time the bandage was exchanged, each of the absorptive wound covering protecting materials was exchanged for new one and its hemostatic effect and wound healing effect at the pin insertion portions were examined. The hemostatic effect and wound healing effect were measured by the extent of fresh bleeding and that of wound contraction at a pin insertion portion as an indicator.

The extent of fresh bleeding and that of wound contraction at a pin insertion portion were classified into four grades (I-IV) such that the higher grade can be recognized to be more effective. The extent of fresh bleeding was indicated by a ratio of a fresh bleeding area to a cross sectional area of a pin (a diameter of 4 mm) of the injury outside fixer. That is, the extent of the fresh bleeding was defined as a grade I when the area of the fresh bleeding portion was twice as large as the pin cross sectional area or larger, as a grade II when the area was as large as the pin cross sectional area or larger but was smaller than twice as large as the pin cross sectional area, as a grade III when the area was half as large as the pin cross sectional area or larger but was smaller than the pin cross sectional area, and as a grade IV when no fresh bleeding portion was recognized. The extent of the wound contraction was indicated by a wound width relative to the diameter of a pin of an injury outside fixer. The wound width was measured as a wound width in a direction perpendicular to an incised direction when inserting a pin and the measurement was performed in the proximity of the edge of the inserted pin. The extent of the wound contraction was defined as a grade I when the wound width was 1.5 times the pin diameter or larger, as a grade II when the width was the same as the pin diameter or larger but was smaller than 1.5 times the pin diameter, as a grade III when the width was half the pin diameter or larger but was smaller than the pin diameter, and as a grade IV when the width was smaller than half the pin diameter. Every time the bandages were exchanged, a grade observation was performed so as to compare the result obtained by the grade observation with that on the immediately preceding observation date (which corresponds the surgery day for the first bandage exchange and the first bandage exchange day for the second bandage exchange). The effect was evaluated by converting the comparisons into numbers such that 1 point was allotted in the case that the grade was increased by one step, 2 points were allotted in the case that the grade was increased by two steps, and 3 points were allotted in the case that the grade was increased by three steps. Each of the evaluation results was obtained by the calculation of total points at three pin insertion portions at a proximal side and a distal side, respectively, with respect to an individual beagle, which was further represented by the mean value of the number of the beagles (n=2 for both the proximal side and the distal side). And then, the evaluation results of pin insertion portions at the distal side of the injury outside fixer are shown in [Table 6], and those of pin insertion portions at the proximal side of the injury outside fixer in [Table 7], respectively. In addition, the evaluation results at the second bandage exchange are scored by addition of the points obtained at the first bandage exchange.

TABLE 6

| | | The present invention products (soluble) | The present invention products (insoluble) |
|---|---|---|---|
| Hemostatic effect | Evaluation of the first bandage Exchange | 3.0 | 2.0 |
| | Evaluation of the second bandage exchange | 5.5 | 5.5 |
| Wound healing effect | Evaluation of the first bandage exchange | 2.0 | 1.5 |
| | Evaluation of the second bandage exchange | 4.5 | 4.5 |

TABLE 7

| | | The present invention products (soluble) | The present invention products (insoluble) |
|---|---|---|---|
| Hemostatic effect | Evaluation of the first bandage Exchange | 2.0 | 0.5 |
| | Evaluation of the second bandage exchange | 6.5 | 4.0 |
| Wound healing effect | Evaluation of the first bandage exchange | 1.5 | 0.0 |
| | Evaluation of the second bandage exchange | 3.5 | 0.5 |

As shown in the above-described [Table 6], it has been observed at the distal side of the pin insertion portion of the injury outside fixer that the soluble absorptive wound covering protecting material of the present invention is somewhat superior to the absorptive wound covering protecting material comprising a sheet-shaped compressed cellulose sponge containing a reinforcement, both in the hemostatic effect and wound healing effect in the evaluations obtained at the first bandage exchange. On the other hand, as shown in the above-described [Table 7], it has been observed at the proximal side of the pin insertion portion of the injury outside fixer that the soluble absorptive wound covering protecting material of the present invention is greatly superior to the absorptive wound covering protecting material comprising a sheet-shaped compressed cellulose sponge containing a reinforcement, both in the hemostatic effect and wound healing effect, in all the evaluations of the bandage exchanges.

In addition, comparing amounts of the exudates from the pin insertion portions at the distal side and the proximal side of the injury outside fixer, an amount of the exudate from the proximal side of the pin insertion portion is generally larger.

This is because soft tissues such as muscles and so on are abound in the proximal side compared to the distal side. It has also been found in such wound area the exudate amount of which is large, that the soluble absorptive wound covering protecting material comprising cellulose fibers wherein hydroxyl groups in a glucose unit constituting a cellulose sponge of the present invention are partly carboxymethylated so that a degree of substitution (a degree of etherification) of the hydroxyl groups is from 0.5 to less than 1.0, has an excellent absorptiveness of the absorptive wound covering protecting material comprising a sheet-shaped compressed cellulose sponge containing a reinforcement, and besides, can be dissolved by the exudade from the wound portion, thereby exhibiting an excellent hemostatic effect on the wound and wound healing effect.

INDUSTRIAL APPLICABILITY

As described above, since the compressed absorptive wound covering protecting material of the present invention is quite excellent in an absorptiveness and a liquid-holding property, it is particularly effective in the case of a large amount of an exudate as in the thin sheet-shaped absorptive wound covering protecting material using the conventional sheet-shaped cellulose sponge. And the compressed absorptive wound covering protecting material of the present invention can resolve the problems of a leakage of the exudate from the wound which makes clothes, sheets or the like foul and unsanitary and of much expense in time and effort for frequent exchanges in order to prevent the exudate from leaking. And besides, since the compressed absorptive wound covering protecting material of the present invention has a high density and an increased strength, it can avoid the possibility that it becomes so soft due to decrease in shape-maintaining ability as to cause tears or deformations therein which make a removing operation difficult when taking off the absorptive wound covering protecting material from the wound, even if the excudate from the wound is absorbed more than necessary.

In addition, for the purpose of enhancing each effect such as an absorptiveness, a liquid-holding property and so on, the compressed absorptive wound covering protecting material of the present invention is not prepared merely by increasing a thickness of the cellulose sponge for use in preparation, that is, merely by increasing an amount of the cellulose sponge to be used. Rather, it is prepared by further compression thereby maintaining an initial certain shape (that is, a sheet-shape), so as to make it possible to prevent difficulty in attachment to the wound, which might be caused by bulkiness due to increase in thickness by increasing an amount of the cellulose sponge to be used, and so as to make it possible to avoid the possibility of contamination and so on of the sterile absorptive wound covering protecting material due to contact with other portions while operating with tweezers. As a result, the attachment of the absorptive covering protecting material for wound can be performed smoothly and sanitarily.

Furthermore, in the case of a cellulose sponge containing a reinforcement, a large particle size of the crystalline mirabilite in a sponge raw solution, specifically a particle size in a range of 0.5 mm to 1.5 mm, results in an appropriately large diameter of the pores (cells) constituting the sponge so as to be able to easily absorb a liquid even with a high viscosity.

Further, as stated above, although the amount of the cellulose sponge used in the compressed absorptive covering protecting material for wound of the present invention is increased, the covering protecting material has a shape-maintaining ability like the thin sheet-shaped absorptive covering protecting material for wound using the conventional cellulose sponge. Therefore, for example, even in the case of attachment to a pin insertion portion of a pin of an injury outside fixer, it is possible to easily fix the wound covering protecting material wherein an incision is formed, by attaching it so as to enter toward the pin. Moreover, even if the wound has swollen, the conventional effect of being able to easily attaching and fixing without pain and without causing any impressions can not be spoiled. In addition, the absorptive wound covering protecting material wherein an incision is formed poses no problem not only to the attachment and fixation to the pin of the above-stated injury outside fixer, but also to the attachment and fixation to drain tubes, tracheotomy tubes, umbilical cords or the like.

Moreover, the compressed absorptive covering protecting material for wound of the present invention can be the one which makes occurrence of fallen fibers difficult (lint-free) as in the case of containing no reinforcement, by selecting the type or shape of the reinforcement even in the case of containing a reinforcement.

Additionally, the compressed and carboxymethylated soluble absorptive wound covering protecting material of the present invention is particularly effective in covering the wound wherein an amount of an exudate is large, since it has an excellent hemostatic effect on the wound and wound healing effect due to its dissolution by the exudate from the wound, in addition to its excellent operational property and absorptiveness which the above-stated compressed absorptive covering protecting material for wound has.

The invention claimed is:

1. An absorptive wound covering protecting material using a cellulose sponge characterized in that the cellulose sponge is prepared by performing a heat treatment on a sponge raw solution that is obtained by mixing viscose containing a reinforcement comprising natural fibers, and crystalline mirabilite as main raw materials, so as to allow the sponge raw solution to be solidified in a thin thickness, and in that the cellulose sponge is formed by compressing the solidified cellulose sponge to be in a sheet form, wherein the reinforcement does not contain at least natural fibers having a length of 1 mm or less.

2. An absorptive wound covering protecting material using a cellulose sponge according to claim 1, wherein the crystalline mirabilite has a particular size of 0.5 mm to 1.5 mm.

3. An absorptive wound covering protecting material using a cellulose sponge characterized in that the cellulose sponge is prepared by performing a heat treatment on a sponge raw solution that is obtained by mixing viscose containing a reinforcement comprising natural fibers, and crystalline mirabilite as main raw materials, so as to allow the sponge raw solution to be solidified in a thin thickness, and in that the cellulose sponge is formed by compressing the solidified cellulose sponge to be in a sheet form, wherein the crystalline mirabilite has a particular size of 0.5 mm to 1.5 mm.

4. An absorptive wound covering protecting material using a cellulose sponge characterized in that the cellulose sponge is prepared by performing a heat treatment on a sponge raw solution containing no reinforcement that is obtained by mixing viscose and crystalline mirabilite as main raw materials, so as to allow the sponge raw solution to be solidified in a thin thickness, and in that the cellulose sponge is formed by compressing the solidified cellulose sponge to be in a sheet form, wherein the cellulose sponge comprises natural or regenerated cellulose fibers where hydroxyl groups in a glucose unit constituting the cellulose molecule are carboxymethylated so that the degree of substitution of the hydroxyl groups is from 0.5 to less than 1.0.

5. A method for preparing an absorptive wound covering protecting material using a cellulose sponge by solidifying a sponge raw solution containing no reinforcement that is obtained by mixing viscose and crystalline mirabilite as main raw materials, in a thickness somewhat greater than a desired thickness by performing a heat treatment in a temperature range of 35° to 70° C. on the sponge raw solution, and then forming the cellulose sponge in a sheet form having a desired thickness by compressing the solidified cellulose sponge, wherein the compressed cellulose sponge is treated with a sodium hydroxide aqueous solution, and then the cellulose sponge is reacted with a monochloroacetic acid solution thereby carboxymethylating hydroxyl groups in a glucose unit constituting a cellulose molecule so that a degree of substitution of the hydroxyl groups is from 0.5 to less than 1.0, and then purifying the cellulose sponge.

6. A method for preparing an absorptive wound covering protecting material using a cellulose sponge according to claim 5, wherein the reaction with a monochloroacetic acid solution is performed for 4 to 18 hours.

7. An absorptive wound covering protecting material using a cellulose sponge characterized in that the cellulose sponge is prepared by performing a heat treatment on a sponge raw solution that is obtained by mixing viscose containing a reinforcement comprising natural fibers, and crystalline mirabilite as main raw materials, so as to allow the sponge raw solution to be solidified in a thin thickness, and in that the cellulose sponge is formed by compressing the solidified cellulose sponge to be in a sheet form, wherein the cellulose sponge comprises natural or regenerated cellulose fibers where hydroxyl groups in a glucose unit constituting the cellulose molecule are carboxymethylated so that the degree of substitution of the hydroxyl groups is from 0.5 to less than 1.0.

* * * * *